United States Patent
Roy et al.

(10) Patent No.: US 9,326,935 B2
(45) Date of Patent: May 3, 2016

(54) ATOMOXETINE SOLUTION

(71) Applicant: Eli Lilly and Company, Indianapolis, IN (US)

(72) Inventors: Arup Kumar Roy, Zionsville, IN (US); Matthew Scott Mermey, Webster, NY (US)

(73) Assignee: Eli Lilly and Company, Indianapolis, IN (US)

( * ) Notice: Subject to any disclaimer, the term of this patent is extended or adjusted under 35 U.S.C. 154(b) by 34 days.

(21) Appl. No.: 14/134,183

(22) Filed: Dec. 19, 2013

(65) Prior Publication Data

US 2015/0133562 A1    May 14, 2015

Related U.S. Application Data

(60) Provisional application No. 61/901,577, filed on Nov. 8, 2013.

(51) Int. Cl.
| | | |
|---|---|---|
| *A61K 9/00* | (2006.01) | |
| *A61K 31/138* | (2006.01) | |
| *A61K 9/08* | (2006.01) | |

(52) U.S. Cl.
CPC .......... *A61K 9/0053* (2013.01); *A61K 9/0095* (2013.01); *A61K 31/138* (2013.01); *A61K 9/08* (2013.01)

(58) Field of Classification Search
CPC ..... A61K 31/138; A61K 9/0053; A61K 9/08; A61K 9/0095
See application file for complete search history.

(56) References Cited

U.S. PATENT DOCUMENTS

| | | | |
|---|---|---|---|
| 2004/0033228 A1* | 2/2004 | Krause et al. ............ 424/145.1 |
| 2005/0096311 A1 | 5/2005 | Suffin et al. | |
| 2005/0152974 A1 | 7/2005 | Boehm et al. | |
| 2007/0134277 A1* | 6/2007 | Chen et al. .................. 424/400 |
| 2007/0207222 A1 | 9/2007 | Yu et al. | |
| 2008/0031932 A1 | 2/2008 | Midha | |
| 2008/0066741 A1 | 3/2008 | LeMahieu et al. | |
| 2008/0145318 A1 | 6/2008 | Midha | |
| 2010/0093827 A1 | 4/2010 | Yu et al. | |
| 2012/0128683 A1 | 5/2012 | Shansha | |
| 2012/0328695 A1 | 12/2012 | Kaiser | |
| 2013/0018059 A1 | 1/2013 | Jacob et al. | |

FOREIGN PATENT DOCUMENTS

| | | |
|---|---|---|
| WO | 2006108120 A1 | 10/2006 |
| WO | 2011075691 A1 | 6/2011 |
| WO | 2012177986 A2 | 12/2012 |

OTHER PUBLICATIONS

Derwent Abstact Equivalent of Chen et al (US 2007/0134277), 2007.*
Fluoxetine Package Insert 2009.pdf.
Jagdish Parasrampuria, et al., Development of oral liquid dosage forms of acetazolamide, Journal of Pharmaceutical Sciences, Sep. 1990, pp. 835-836,vol. 79, Issue 9.
Y. Deepthi Priya, et al., An approach for taste masking of bitter drug atomoxetine HCl, International Journal of Advances in Pharmaceutical Research, Apr. 2011, pp. 119-121, vol. 2, Issue 4.
X20145 International Search Report and Written Opinion of the International Search Authority, (2014).

* cited by examiner

*Primary Examiner* — Savitha Rao
*Assistant Examiner* — Angela Brown-Pettigrew
(74) *Attorney, Agent, or Firm* — Robert D. Titus; Zhiyang Rao

(57) ABSTRACT

The present invention provides a novel palatable pharmaceutical composition in the form of aqueous solution of atomoxetine. The oral aqueous solution of this invention will significantly reduce the potently bitter taste of atomoxetine, and further avoid swallow issue for young and elderly patients.

7 Claims, No Drawings

ATOMOXETINE SOLUTION

The present invention relates to pharmaceutical compositions in the form of aqueous oral solutions of atomoxetine wherein the potently bitter taste of atomoxetine is substantially reduced. The pharmaceutical compositions are particularly useful for administration to children and adolescents being treated for attention deficit hyperactivity disorder (ADHD) with atomoxetine.

Atomoxetine in this invention means atomoxetine per se, which is (−)-N-methyl-3-phenyl-3-(o-tolyloxy)propylamine, or a pharmaceutically accepted salt thereof. The particular salt in this invention is atomoxetine hydrochloride.

Gehlert et al. ((1993) *Neuroscience Letters* 157:203-206) discussed atomoxetine's activity as a selective norepinephrine reuptake inhibitor. As disclosed in U.S. Pat. No. 5,658,590, atomoxetine can be used to treat ADHD in children, adolescents and adults. Eli Lilly and Company currently markets atomoxetine hydrochloride under the name Strattera® in the form of capsules of different dosage strengths for this purpose.

The currently available atomoxetine hydrochloride solid dosage form, which is a capsule, is acceptable for the treatment purpose. However, this solid dosage form and the potently bitter taste of atomoxetine impose serious compliance problems in patients who are unable or unwilling to take the current solid dosage form of this compound. The solid dosage form is generally difficult for young children and elderly patients to swallow. The potently bitter taste makes it even harder to administer especially for young patients. Although there are many methods to suppress certain undesired taste of drugs, there is no universal formulation capable of solving this problem due to the unique properties of different drugs.

Currently, there is no reported development of a taste-masked oral solution formulation for atomoxetine. Boehm et al provided in US 2005/0152974 extensive coverage for a variety of atomoxetine formulations such as wax, press-coat, sprinkle, chewable, controlled release and liquid dosages. The liquid dosage formulation disclosed in this patent application is a suspension instead of a homogeneous solution. There is a need to develop a palatable solution dosage form of atomoxetine to reduce or eliminate its potently bitter taste, and to avoid the difficulty in swallowing solid dosage forms such as tablets and capsules.

The technique to use sweetening and flavoring agents to enhance drug taste is one of the most widely used approaches for taste masking, especially in the case of pediatric formulations such as chewable tablets and liquid formulations. However, this approach is not very successful for highly bitter and highly water soluble drugs. See, for example, Approaches of taste masking. Vishani et al, *International Journal of Pharmacy and Integrated Life Sciences*, April 2013, Vol 1 (5). p 48-61. Atomoxetine is a well-known highly bitter and highly water soluble drug. In addition, atomoxetine has prolonged bitter taste. Thus, it is expected to be very challenging to make an acceptable palatable solution dosage form of atomoxetine.

However, the present invention surprisingly provides pharmaceutical compositions of oral aqueous atomoxetine solutions. The atomoxetine aqueous solutions provide compliant dosage forms especially useful in pediatric and child populations.

The present invention provides pharmaceutical compositions of oral aqueous solutions comprising atomoxetine and water.

The present invention provides pharmaceutical compositions of oral aqueous solutions comprising atomoxetine, water, and a flavoring agent.

The present invention provides pharmaceutical compositions of oral aqueous solutions comprising atomoxetine, water, a flavoring agent, and a sweetening agent.

The present invention provides pharmaceutical compositions of oral aqueous solutions comprising atomoxetine, water, a flavoring agent, and a sweetening agent, wherein the pH of the oral atomoxetine solutions is in the range of 2.0 to 6.0.

The present invention provides pharmaceutical compositions of oral aqueous solutions comprising atomoxetine, water, a flavoring agent that is F-9999 PFC Artificial Raspberry CA Flavor, and a sweetening agent, wherein the pH of the oral atomoxetine solutions is in the range of 2.0 to 6.0.

The present invention provides pharmaceutical compositions of oral aqueous solutions comprising atomoxetine, water, F-9999 PFC Artificial Raspberry CA Flavor, and a sweetening agent, wherein the pH of the oral atomoxetine solutions is in the range of 2.0 to 6.0, and the concentration of F-9999 PFC Artificial Raspberry CA Flavor is in the range of 1.0-30 mg/mL.

The present invention provides pharmaceutical compositions of oral aqueous solutions comprising atomoxetine, water, sodium benzoate, sodium dihydrogen phosphate dihydrate, phosphoric acid, sorbitol, xylitol, F-9999 PFC Artificial Raspberry CA Flavor, and sucralose, wherein the pH of the oral atomoxetine solutions is in the range of 3.0 to 5.0.

The present invention provides pharmaceutical compositions of oral aqueous solutions comprising atomoxetine, water, sodium benzoate, sodium dihydrogen phosphate dihydrate, phosphoric acid, sorbitol, xylitol, F-9999 PFC Artificial Raspberry CA Flavor, and sucralose, wherein the more preferable pH of the oral atomoxetine solutions is in the range of 3.7-4.3.

The present invention provides pharmaceutical compositions of oral aqueous solutions comprising atomoxetine, water, sodium benzoate, sodium dihydrogen phosphate dihydrate, phosphoric acid, sorbitol, xylitol, F-9999 PFC Artificial Raspberry CA Flavor, and sucralose, wherein the pH of the oral atomoxetine solutions is in the range of 3.7-4.3, and the concentration of atomoxetine is in the range of 0.1 to 25 mg/mL.

The present invention provides pharmaceutical compositions of oral aqueous solutions comprising atomoxetine, water, sodium benzoate, sodium dihydrogen phosphate dihydrate, phosphoric acid, sorbitol, xylitol, F-9999 PFC Artificial Raspberry CA Flavor, and sucralose, wherein the pH of the oral atomoxetine solutions is in the range of 3.7-4.3, and the more preferable concentration of atomoxetine is in the range of 1.0 to 10.0 mg/mL.

The present invention provides pharmaceutical compositions of oral aqueous solutions comprising atomoxetine, water, sodium benzoate, sodium dihydrogen phosphate dihydrate, phosphoric acid, sorbitol, xylitol, F-9999 PFC Artificial Raspberry CA Flavor, and sucralose, wherein the pH of the oral atomoxetine solutions is in the range of 3.7-4.3, and the most preferable concentration of atomoxetine is in the range of 3.0 to 6.0 mg/mL.

The present invention provides pharmaceutical compositions of oral aqueous solutions comprising atomoxetine hydrochloride, water, sodium benzoate, sodium dihydrogen phosphate dihydrate, phosphoric acid, sorbitol, xylitol, F-9999 PFC Artificial Raspberry CA Flavor, and sucralose, wherein the pH of the oral atomoxetine solutions is in the range of 3.7-4.3, and the most preferable concentration of atomoxetine is in the range of 3.0 to 6.0 mg/mL.

The present invention also provides a method of treating attention deficit hyperactivity disorder in a patient, comprising orally administering to the patient in need of such treatment an effective amount of a pharmaceutical composition of atomoxetine oral aqueous solution.

The present invention further provides pharmaceutical compositions of atomoxetine oral aqueous solution described herein, for the use in the manufacture of medicament to treat attention deficit hyperactivity disorder.

The present invention also provides a process to make a pharmaceutical composition of oral aqueous solution by combining atomoxetine, water, sodium benzoate, sodium dihydrogen phosphate dihydrate, phosphoric acid, sorbitol, xylitol, F-9999 PFC Artificial Raspberry CA Flavor, and sucralose, and maintaining a pH in the range of 3.7-4.3 to form a solution.

The present invention also provides a process to make a pharmaceutical composition of oral aqueous solution by combining atomoxetine hydrochloride, water, sodium benzoate, sodium dihydrogen phosphate dihydrate, phosphoric acid, sorbitol, xylitol, F-9999 PFC Artificial Raspberry CA Flavor, and sucralose, and maintaining a pH in the range of 3.7-4.3 to form a solution.

The present invention also provides a process to make a pharmaceutical composition of an oral aqueous solution, comprising the following steps:
(a). adding atomoxetine hydrochloride, sodium benzoate, and sodium dihydrogen phosphate dihydrate to purified water, and stir until a solution is formed;
(b). adding phosphoric acid that is diluted in purified water to the solution formed in step (a), and stir until a solution is formed;
(c). adding sorbitol to the solution formed in step (b), and stir until a solution is formed;
(d). adding xylitol to the solution formed in step (c), and stir until a solution is formed;
(e). adding flavoring agent F-9999 PFC Artificial Raspberry CA Flavor to the solution formed in step (d), and stir until a solution is formed;
(f). adding sucralose to the solution formed in step (e), and stir until a solution is formed;
(g). adjusting pH of the solution formed in step (f) to 3.7 to 4.3 with aqueous phosphoric acid solution and/or aqueous sodium hydroxide solution; and
(h). adding purified water to the solution formed in step (g) to achieve the atomoxetine hydrochloride concentration in the range of 3.0 to 6.0 mg/mL.

The present invention also provides a pharmaceutical composition of an atomoxetine solution prepared by the process comprising the following steps:
(a). adding atomoxetine hydrochloride, sodium benzoate, and sodium dihydrogen phosphate dihydrate to purified water, and stir until a solution is formed;
(b). adding phosphoric acid that is diluted in purified water to the solution formed in step (a), and stir until a solution is formed;
(c). adding sorbitol to the solution formed in step (b), and stir until a solution is formed;
(d). adding xylitol to the solution formed in step (c), and stir until a solution is formed;
(e). adding flavoring agent F-9999 PFC Artificial Raspberry CA Flavor to the solution formed in step (d), and stir until a solution is formed;
(f). adding sucralose to the solution formed in step (e), and stir until a solution is formed;
(g). adjusting pH of the solution formed in step (f) to 3.7 to 4.3 with aqueous phosphoric acid solution and/or aqueous sodium hydroxide solution; and
(h). adding purified water to the solution formed in step (g) to achieve the atomoxetine hydrochloride concentration in the range of 3.0 to 6.0 mg/mL.

The pharmaceutical compositions in the form of aqueous oral atomoxetine solution in this invention successfully mask the bitterness of atomoxetine, while providing acceptable mouthfeel and aftertaste.

In addition to the improved taste, the oral aqueous solutions in this invention provide a stable shelf-life at room temperature of at least about 24 months.

Administration of the aqueous solutions of the present invention is achieved by introducing an appropriate volume of aqueous solution of atomoxetine in the mouth, which the patient then swallows. Alternatively, such solutions can be mixed with foods or beverages if preferred.

All flavoring agents used in the present invention are commercially available through Foote and Jenks, which is also known as Pharmaceutical Flavor Clinic in Camden, N.J.

The following examples are given by way of illustration only, and are not to be construed as a limitation in any way of this invention, many variations of which are possible within the scope thereof.

EXAMPLE 1

Atomoxetine Solution with Raspberry CA Flavor

An oral aqueous atomoxetine solution according to the invention is prepared by mixing the following ingredients in Table 1.

TABLE 1

Oral Aqueous Atomoxetine Solution Ingredients, Concentrations and Functions of Ingredients

| Ingredient | Concentration (mg/mL) | Function |
| --- | --- | --- |
| Atomoxetine Hydrochloride (Equivalent Free Base) | 4.6 (4.0) | Active Ingredient |
| Sodium Benzoate | 0.8 | Preservative |
| Sodium Dihydrogen Phosphate Dihydrate | 17.0 | Buffer |
| Phosphoric Acid | 0.6 | Buffer |
| Sorbitol Solution ("70% w/w") | 47.1 | Sweetener |
| Xylitol | 300.0 | Sweetener |
| F-9999 PFC Artificial Raspberry CA Flavor | 14.7 | Flavoring Agent |
| Sucralose Powder | 10.0 | Sweetener |
| Purified Water [1] | Carrier, make the total solution to 1.0 mL | Vehicle |

[1] Sodium hydroxide and/or additional phosphoric acid are optional and may be used only if necessary to adjust pH to the desired range of 3.7 to 4.3 prior to the final addition of purified water to reach the desired atomoxetine concentration.

Add purified water (310 kg) to a suitable manufacturing vessel with maintained temperature at about 42° C., and followed by the addition of atomoxetine hydrochloride (2.30 kg). Stir until the atomoxetine hydrochloride is dissolved. Add sodium benzoate (0.40 kg) and stir until sodium benzoate is dissolved. Add sodium dihydrogen phosphate dihydrate (8.5 kg) and stir until it is dissolved to form the main solution.

Dilute concentrated phosphoric acid (0.31 kg) with purified water to make a 10% (w/w) phosphoric acid aqueous solution in a separate mixing vessel. Add the phosphoric acid aqueous solution to the previously prepared main solution and stir. And then add sorbitol aqueous solution (70% (w/w), 23.55 kg) to the solution and stir. Maintain the temperature at about 42° C. Then add xylitol (150 kg) to the formed solution and stir until solid is dissolved, while maintaining the temperature of the solution at this step at from 20 to 30° C. with necessary heating or cooling.

Add the flavoring agent F-9999 PFC Artificial Raspberry CA Flavor (7.35 kg) to the above formed solution and stir. Then add sucralose powder (5.0 kg) and stir until solid is dissolved. Adjust the pH of the solution if necessary with the phosphoric acid aqueous solution (10% (w/w)) and/or sodium hydroxide solution (an approximate 4% (w/w)). Maintain the temperature of the solution at from 20 to 30° C. Make a final in-process check of pH to verify that the pH is within the range of 3.7-4.3. Add sufficient quantity of purified water to the formed solution of pH 3.7-4.3 to achieve the final solution with a concentration of 4.6 mg/mL by atomoxetine hydrochloride or 4.0 mg/mL by atomoxetine free base.

Filter the solution by an in-line polypropylene filter with a 4.5 micron pore opening into a holding vessel to provide a clear homogeneous solution.

EXAMPLE 2

| Atomoxetine Solution Unflavored | | |
|---|---|---|
| Ingredient | Concentration (mg/mL) | Function |
| Atomoxetine Hydrochloride (Equivalent Free Base) | 4.6 (4.0) | Active Ingredient |
| Sorbitol Solution, Non-Crystallizing | 50 | Sweetener |
| Xylitol | 300 | Sweetener |
| Sucralose | 10 | Sweetener |
| Sodium Phosphate Monobasic Monohydrate | 15 | Buffer |
| Phosphoric Acid Solution 0.425M | 12.5 | Buffer |
| Sodium Benzoate | 1.0 | Preservative |
| Purified Water[2] | Carrier, make the total solution to 1.0 mL | Vehicle |

[2]Sodium hydroxide and/or additional phosphoric acid are optional and may be used only if necessary to adjust pH to the desired range of 3.7 to 4.3 prior to the final addition of purified water to reach the desired atomoxetine concentration.

EXAMPLE 3

Atomoxetine Solution with Raspberry Cream Flavor

An oral atomoxetine solution according to the invention is prepared as in Example 2. The formulation is the same, except for the addition of 4.5 mg of Raspberry Cream Flavor PFC 9929, 2.5 mg of Vanilla Flavor F-9760, 2.5 mg of Bitter Mask Flavor PFC 9885, and 3.0 mg of Mint Menthol Flavor PFC 9895.

EXAMPLE 4

Atomoxetine Solution with Fruity Flavor

An oral atomoxetine solution according to the invention is prepared as in Example 2. The formulation is the same, except for the addition of 4.5 mg of Fruity Flavor PFC 9975, and 3.0 mg of Mint menthol Flavor PFC 9895.

EXAMPLE 5

Atomoxetine Solution with Raspberry Flavor

An oral atomoxetine solution according to the invention is prepared as in Example 2. The formulation is the same, except for the addition of 17.25 mg of F-9999 PFC Artificial Raspberry CA Flavor.

Flavor Test

The flavor test results are based on the analysis of 3-6 highly trained judges who are experienced in detailed flavor analysis. The descriptive analysis methodology is characterized in the following Table 2. The test results are illustrated in the following Table 3.

TABLE 2

| Flavor Scale | | | | | | |
|---|---|---|---|---|---|---|
| Flavor Scale | 0 to 1 | 1.1 to 3 | 3.1 to 6 | 6 to 9 | 9 to 12.5 | >12.5 |
| Description | Very Slight; Barely discernible | Slight | Slight to Moderate | Moderate | Moderate to High | High |

TABLE 3

| Flavor Spectrum Profiles for Atomoxetine Solutions (Example 2 to 5) | | | | |
|---|---|---|---|---|
| | Examples and Flavors | | | |
| | Example 2 | Example 3 | Example 4 | Example 5 |
| Sweet (Basic Taste) | 12.0 | 17.0 | 14.0 | 11.0 |
| Bitter (Basic Taste) | 10.0 | 4.0 | 5.0 | 1.5 |
| Sweet (Aftertaste) | 7.0 | 6.5 | 6.5 | 8.0 |
| Bitter (Aftertaste) | 18.0 | 7.5 | 10.0 | 2.0 |

The analysis results in Table 3 illustrate the effectiveness of different flavoring agents in the masking of the potent bitterness. The samples are prepared with essentially the same method except the addition of different flavoring agents.

The atomoxetine solution with F-9999 PFC Artificial Raspberry CA Flavor in Example 5 provides the most preferable taste comparing with the unflavored (Example 2), Raspberry Cream flavored (Example 3), and Fruity flavored (Example 4) atomoxetine solutions.

The bitter-masking agents do not interfere with the effectiveness of the flavoring and sweetening agents in improving the taste of atomoxetine solutions, and none of these excipients adversely affects the medicinal effectiveness of atomoxetine. Such palatable atomoxetine formulations should prove useful in improving patient compliance in pediatric and child populations being treated for ADHD with this pharmaceutical agent.

We claim:

1. A pharmaceutical composition comprising 0.1-25 mg/mL atomoxetine, water, 1-30 mg/mL F-9999 PFC Artificial Raspberry CA Flavor, and a sweetening agent, wherein the pharmaceutical composition is in the form of a clear homogeneous oral aqueous solution, and the pH of the clear homogeneous oral aqueous solution is in the range of 2.0 to 6.0.

2. A method for treating attention-deficit/hyperactivity disorder (ADHD), comprising orally administering to a patient an effective amount of the pharmaceutical composition as claimed in claim 1.

3. The pharmaceutical composition as claimed in claim 1, wherein the concentration of atomoxetine is in the range of 3-6 mg/mL.

4. The pharmaceutical composition as claimed in claim 3, wherein the pH is in the range of 3.7-4.3.

5. The pharmaceutical composition as claimed in claim 4, wherein atomoxetine is atomoxetine hydrochloride.

6. The pharmaceutical composition as claimed in claim 5, further comprising sodium benzoate, sodium dihydrogen phosphate dihydrate, phosphoric acid, sorbitol solution, xylitol, and sucralose powder.

7. The pharmaceutical composition as claimed in claim 6, comprising 4.6 mg/mL atomoxetine hydrochloride, 0.8 mg/mL sodium benzoate, 17.0 mg/mL sodium dihydrogen phosphate dihydrate, 0.6 mg/mL phosphoric acid, 47.1 mg/mL sorbitol solution (70% w/w), 300.0 mg/mL xylitol, 14.7 mg/mL F-9999 PFC Artificial Raspberry CA Flavor, and 10.0 mg/mL sucralose powder.

* * * * *